United States Patent [19]

Wesseling

[11] Patent Number: 4,510,940
[45] Date of Patent: Apr. 16, 1985

[54] PLETHYSMOGRAPH PRESSURE CORRECTING ARRANGEMENT

[75] Inventor: Karel H. Wesseling, Bunnik, Netherlands

[73] Assignee: Nederlandse Centrale Organisatie Voor Toegepast-Natuurwetenschappelijk Onderzoek, The Hague, Netherlands

[21] Appl. No.: 444,363

[22] Filed: Nov. 26, 1982

[30] Foreign Application Priority Data

Nov. 27, 1981 [NL] Netherlands ................. 8105381

[51] Int. Cl.³ .................................................. A61B 5/02
[52] U.S. Cl. ....................................... 128/667; 128/681
[58] Field of Search ............................... 128/665–667, 128/680–681, 672, 677, 687, 691

[56] References Cited

U.S. PATENT DOCUMENTS

| | | | |
|---|---|---|---|
| 3,585,987 | 6/1971 | Svensson | 128/672 |
| 4,105,021 | 8/1978 | Williams et al. | 128/683 |
| 4,406,289 | 9/1983 | Wesseling et al. | 128/672 X |

FOREIGN PATENT DOCUMENTS

2070240 9/1981 United Kingdom ............... 128/666

Primary Examiner—Lee S. Cohen
Assistant Examiner—Angela D. Sykes
Attorney, Agent, or Firm—Cushman, Darby and Cushman

[57] ABSTRACT

A method and a device for correcting the cuff pressure in the indirect, non-invasive and continuous measurement of the blood pressure in a part of the body by using a plethysmograph in a fluid-filled pressure cuff, an electronic control circuit, and an electric pressure valve. The cuff pressure is controlled by the plethysmographic signal in closed-loop operation with the aid of a servo-reference level obtained via a memory circuit. The servo-reference level, in operation of the device, is adjusted by opening the closed loop of the control circuit for a short interval, after which, in open-loop operation the cuff pressure is adjusted at an intermediate pressure derived from the pressure last measured and the servo-reference level is adjusted via the memory circuit.

33 Claims, 13 Drawing Figures

PLETHYSMOGRAPH PRESSURE CORRECTING ARRANGEMENT

The invention relates to a method for correcting the cuff pressure in the indirect, non-invasive and continuous measurement of the blood pressure in a part of the body by using a plethysmograph in a fluid-filled pressure cuff, an electronic control circuit, and an electric pressure valve, the cuff pressure being controlled by the plethysmographic signal in closed-loop operation with the aid of a servo-reference level obtained via a memory circuit, which servo-reference level is initially adjusted such that the cuff pressure corresponds substantially with the momentary arterial pressure. The invention, furthermore, relates to a device to carry out this method, which device comprises a plethysmograph in a fluid-filled pressure cuff, an electric pressure valve, and an electronic control circuit provided with a control loop having a differential amplifier and memory circuit in the feedback circuit for the servo-reference level, and with a control loop having a proportionate, integrate and differentiate (PID) circuit, a parallel circuit of peak detector and trough detector for the pressure signal, which parallel circuit is responsive to the pressure in the pressure cuff, and a state switch for closed-open loop operation. Such a method and device are known from U.S. patent application Ser. No. 437,026, filed Oct. 27, 1982.

In the method and device described in the abovementioned Netherlands patent application the pressure of the fluid, e.g. air, in the pressure cuff around a part of the body, such as a finger, is controlled on the basis of the signal of the plethysmograph by the electric pressure valve, controlled by a servo loop. This control is such that at any moment the difference between a servo-reference level or nominal value and the plethysmographic signal or real value—but for a servo-rest error—equals zero. The servo-reference level in this method and device is initially adjusted automatically such that the cuff pressure continuously corresponds substantially with the momentary arterial pressure under the cuff both for pulsations and for absolute pressure level. Consequently, this arterial pressure can be read from the fluid pressure in the pressure cuff.

In practice it has turned out that the servo-reference level for a correct measurement of the blood pressure drifts with time. This can for instance be ascertained by comparing the cuff pressure with a blood pressure measured in a conventional manner invasively in a nearby artery. After the initial adjustment corresponding blood pressures are measured in the beginning. After some lapse of time, for instance between 10 and 1000 seconds, the cuff pressure is higher, but mostly lower than the invasively measured blood pressure. After a repeated adjustment, the blood pressure level appears to be measured correctly again, in which case the new servo-reference level deviates from the preceding level. This shift is effected by (patho-)physiological causes, such as a change in the tonus of the smooth muscle tissue in the arterial vascular wall. Due to this a change, like a contraction, can occur in the unstretched volume of the arteries.

While measuring the blood pressure of normal healthy persons and after an adjustment carried out once or twice a servo-reference level is obtained by which it is further possible to measure correct blood pressures for a long space of time, say 30 to 60 minutes. However, in case of patients, whose blood circulation is heavily stressed, such as under anesthesia, when undergoing an operation or in case of blood-letting, the period of correct blood pressure recording will become shorter. It may be accompanied by a gradual shift in the cuff pressure, an abrupt drop-off of the cuff pressure or a sudden sharply increasing cuff pressure with respect to the invasive measurement.

In order to avoid such errors in the measurement of cuff pressure, which can confuse the medical attendants, it would be necessary to repeat the adjustment procedure every twenty to thirty seconds. With a typical initial adjustment time of fifteen seconds there remains but little working time. Then one can no longer speak of a continuous and reliable measurement of blood pressure.

The object of the invention is to provide a method and device for the automatic correction of the cuff pressure by adjusting the servo-reference level such that a correct measurement is continuously guaranteed at the expense only of a very slight loss percentage of time.

This object is attained by providing an arrangement whereby the servo-reference level is adjusted by opening the closed loop of the control circuit for a short interval. In open-loop operation the cuff pressure is adjusted at an intermediate pressure derived from the pressure last measured and the servo-reference level is adjusted via the memory circuit. This adjustment of the servo-reference level can be carried out regularly and automatically, such as once in a period of twenty to thirty seconds. In a further aspect of the invention, the servo-reference level can be adjusted in dependence of the form of the plethysmographic signal influenced by the magnitude of the deviation of the cuff pressure, adjusted in open-loop operation, with respect to the real arterial pressure.

Furthermore, the device mentioned in the preamble for carrying out the above method, is characterized in that the peak detector and trough detector for the pressure signal is followed by a conversion circuit, which derives an intermediate value from the peak and/or trough amplitude values of the pressure signal in closed-loop operation, that a timing circuit is provided to switch the state switch for a short interval from closed-loop position to open-loop position, whereby the intermediate value is supplied via the state switch to the electric pressure valve, and the memory circuit adjusts the servo-reference level such that the average difference at the differential amplifier is zero.

The method and the device according to the invention can be used to advantage in combination with a photo-electric plethysmograph in a pressure cuff around a part of the body, such as a finger, whereby the quantity of light transmitted therein is measured. But they can also be used in combination with an electric impedance plethysmograph in a pressure cuff around a part of the body, such as an upper arm, whereby the electric impedence is measured.

The invention will be explained in detail on the basis of some embodiments with reference to the drawings, in which like or corresponding elements in the various figures are indicated by the same reference numbers, and in which.

Figure 1:
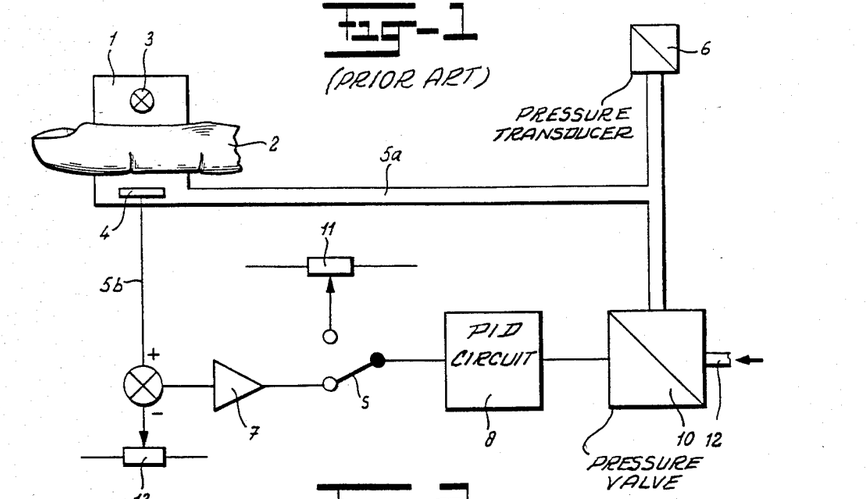
FIG. 1 shows a simplified block diagram of the device used in the known method.

The known device shown in FIG. 1 has a photo-electric plethysmograph in a pressure cuff 1 mounted around the finger 2, which pressure cuff is provided on the inside with a light source 3 and a light detector 4. The plethysmographic or volume-changing signal outputted by the light detector 4 is supplied via line 5b to a differential amplifier 7, to which also an adjustment or servo-reference level is supplied from the adjustment means 13. The output signal of the differential amplifier 7 is supplied in closed-loop operation of a switch S to a PID circuit 8. In open-loop operation, i.e. at opened control loop, a pressure adjusting signal is supplied from the manual adjustment means 11 to the PID circuit 8. State switch S can alternatively be placed after the PID circuit. The output signal of the PID circuit controls the electric pressure valve 10 such that the fluid, such as air, of the compressor 12 is adjusted to the desired pressure which is conveyed via line 5a to the pressure cuff 1. The pressure can be read or recorded with the aid of a pressure transducer 6 connected to the output of the electric pressure valve 10.

Figure 2:
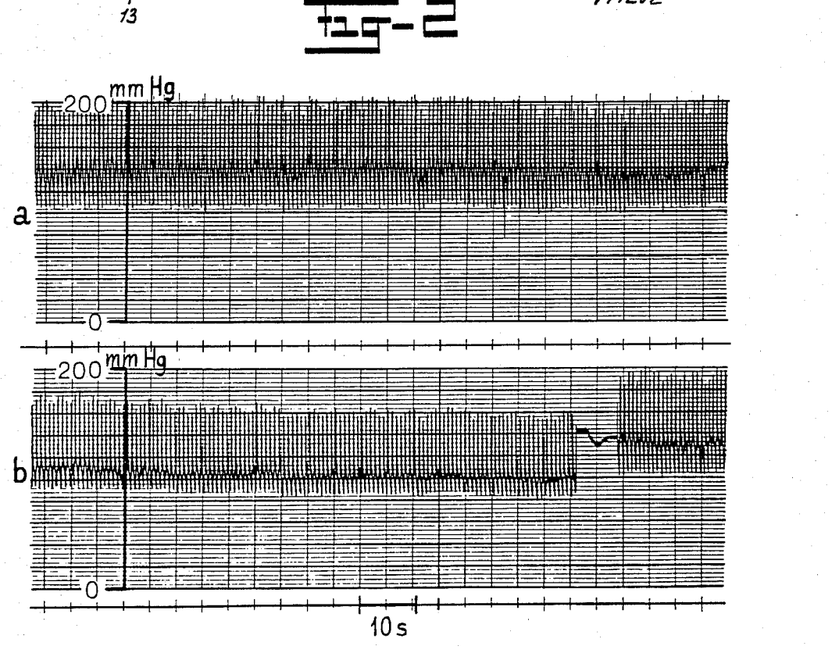
FIG. 2 shows a comparative record of a non-invasively measured blood pressure in a finger and of a blood pressure in a nearby artery measured invasively in a conventional way.

FIG. 2 shows, with respect to time, on line a the blood pressure of a patient during a conventional invasive measurement in an artery not far from the finger in question. A non-invasive blood pressure measurement of the finger is shown, with respect to time, on line b. From FIG. 2b it appears that in the measurement of the blood pressure in the finger a cuff pressure is measured which, after some time, drifts with respect to the invasively measured blood pressure according to FIG. 2a. A correct blood pressure level is measured anew, when, as shown on the right in FIG. 2b, the initial adjustment procedure is repeated. Thereby, however, the new servo-reference level appears to deviate from the preceding one, which deviation is effected by (patho-)physiological causes. This can cause a change, for example a contraction, in the unstretched volume of the arteries.

Such a contraction can occur within a time period of ten seconds. This drift of the cuff pressure occurs especially in cases, in which the blood circulation is heavily loaded, such as when the patient is under anesthesia, undergoes an operation or has his blood tapped. This can take place either suddenly at odd moments or gradually.

Figure 3:
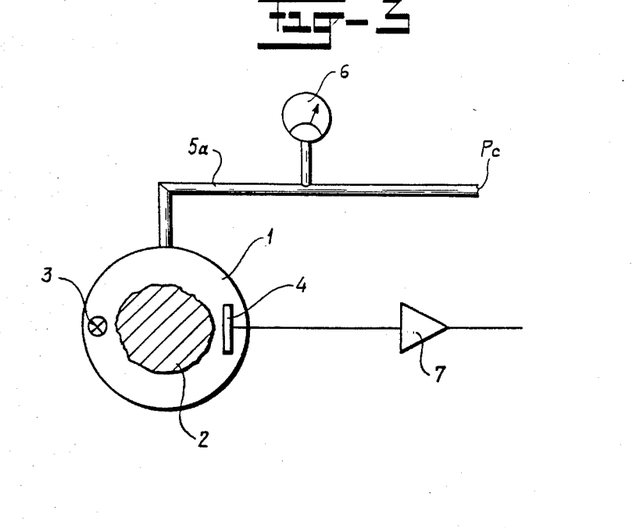
FIG. 3 shows a schematic arrangement of a photoelectric plethysmograph around a finger with unloaded artery wall.

FIG. 3 schematically shows the photo-electric plethysmograph. The fluid, e.g. air, is supplied at a pressure $P_c$ via line 5a to the pressure cuff 1 around the finger 2 shown in cross-section. The light from the light source 3, such as a light-emitting diode, is partly transmitted via the tissue to a light detector 4 such as a light-sensitive diode. The latter may be back-biased by a voltage source due to which the current strength is proportionate to the intensity of the light incident on the light detector.

The tissue in the finger is diffusely illuminated by the light source. Part of the light is intercepted, i.e. absorbed or dispersed by the red blood corpuscles in the blood vessels, mainly the two arteries, between light source and light detector. Another part passes the tissue, which is not perfused anymore due to the cuff pressure $P_c$ at the outside, and strikes the light detector.

Figure 4:
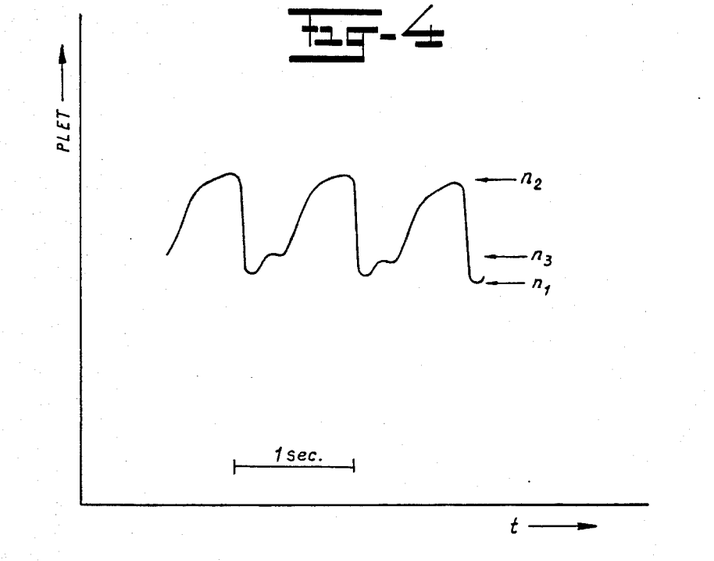
FIG. 4 shows an example of the plethysmographic signal at a given constant cuff pressure.

The plethysmographic signal outputted by the amplifier 7 is set out in FIG. 4 as a function of time at a pressure $P_c$ exerted on the pressure cuff. The two arteries in the finger are not collapsed when the intra-arterial pressure is higher than the extra-mural tissue pressure, which at a correct approximation equals the cuff pressure. In this state a relatively small quantity of light reaches the light detector as represented by the minima around level $n_1$ in the plethysmogram of FIG. 4. When, on the other hand, the arteries are collapsed a relatively large quantity of light reaches the photocell as represented by the maxima around level $n_2$ in the plethysmogram of FIG. 4. So, when the cuff pressure is adjusted to a level value between the maximal or systolic and the minimal or diastolic blood pressure, then alternately a positive and a negative pressure difference will occur over the arterial wall. The arteries will consequently collapse and open periodically. The quantity of light reaching the photo-cell will vary with time, as shown in FIG. 4, as the attenuation of the light is proportionate to the total arterial blood-filled cross-section. Also in FIG. 4 an intermediate level $n_3$ of the amount of light reaching the photo-cell is indicated, which represents the just open or unstretched artery.

When the correct servo-reference level of the servo-control loop is somewhere between the open and the collapsed level, then an incorrect measurement will follow as soon as the quantity of dispersed light changes without the servo-reference level being adapted. Also, when the correct servo-reference level is at a fraction equal to $(n_3-n_1)/(n_2-n_1)$ between open and collapsed state and the difference between these levels should change swiftly, the servo-reference level will have to be adapted for a correct blood pressure measurement. The invention corrects these causes of potential errors by means of an automatic adjustment of the servo-reference level during a short interruption in the continuous measurement.

Figure 5:
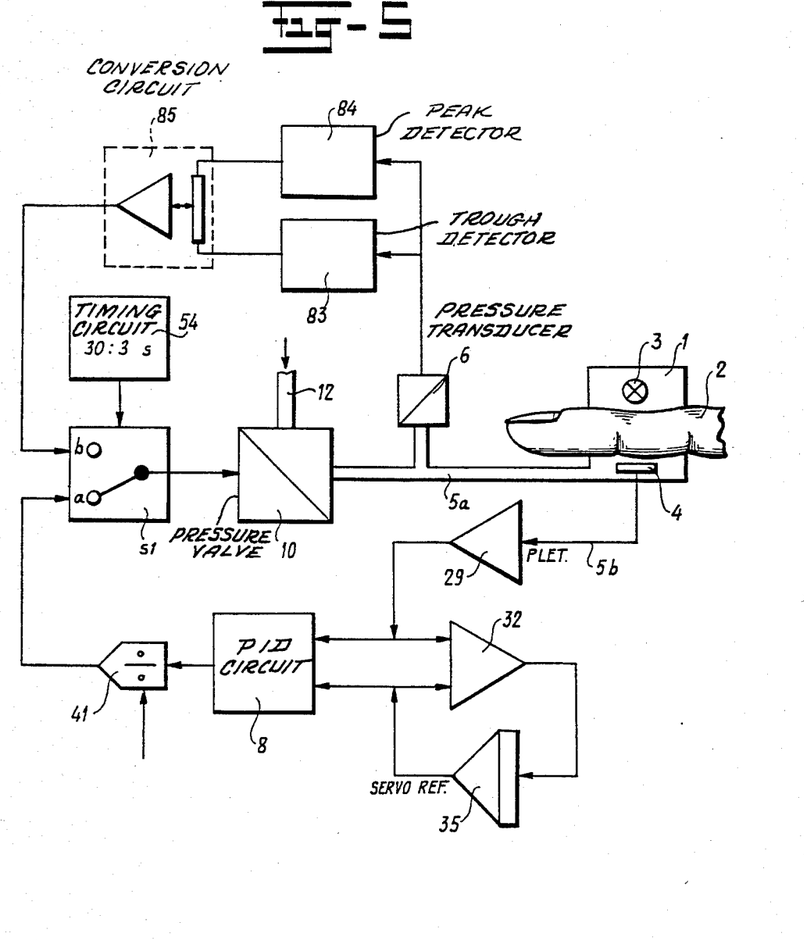
FIG. 5 shows a diagram of an embodiment of the device according to the invention.

FIG. 5 shows a diagram of an embodiment of the device to carry out this automatic adjustment. The plethysmographic signal from the amplifier 29 is supplied as a real value to a control loop consisting of the differential amplifier 32 and memory circuit 35 and to an input of the PID circuit 8 taken up in a further control loop. The memory circuit 35 can advantageously consist of an integration circuit. The output signal of the PID circuit 8 is supplied via a circuit 41 for setting the loop gain and implemented as a divider, to an input a of the state switch S1. In closed-loop operation this signal is converted, via the electric pressure valve 10 provided with air from compressor 12, into pressure which is conveyed via line 5a to the pressure cuff 1.

In this embodiment according to the invention the servo-reference level can be adjusted in a so-called passive one-step procedure. This starts from the view that it is less important at what pressure level between systolic and diastolic level the cuff pressure in open-loop operation is adjusted as over a range of cuff pressures the arteries under the cuff after all will periodically open and collapse.

In the closed-loop position a of the state switch S1, the constant servo-reference level or nominal value is provided by the memory circuit 35 as any difference between real and nominal value at the differential circuit 32 is readjusted to zero by the fast control loop via the PID circuit.

The parallel circuit of peak detector 84 and trough detector 83 connected to the pressure transducer 6 determines at each heart beat the systolic and the diastolic pressure in the blood pressure signal.

Immediately after termination of the detection by the two detectors 83, 84 an intermediate value between the peak and trough amplitude values is derived by a succeeding conversion circuit 85. This intermediate value is supplied to the state switch S1. The conversion circuit 85 can advantageously consist of a resistance divider having an adjustable tap and a succeeding buffer amplifier. In this way a signal value can be obtained which lies a fixed or variable part of the peak-trough amplitude difference above the trough amplitude. The conversion circuit can also consist of a summing circuit and a succeeding two-divider so that a (Psyst+Pdias)/2 value is obtained. The state switch S1 is set in the open-loop position b for a short interval of e.g. three seconds at times predetermined by the timing circuit 54, e.g. once per thirty seconds or manually by an observer.

The intermediate pressure, determined by the conversion circuit 85 between the last perceived systolic and diastolic pressure levels, is supplied in this open-loop position to the cuff and is maintained for three seconds. The memory circuit 35 can adjust its output (servo-reference) level during this interval such that the average difference at the differential amplifier 32 is zero. After this, the state switch S1 is reset in the closed-loop position a.

It is possible to synchronize the moment of switching from closed to open-loop operation after the course of time, determined by the timing circuit, with the heart beat, e.g. detected by the peak detector and trough detector.

This adjustment requires relatively little time and only few heart beats are lost. In case, however, larger variations start to occur in the correct servo-reference level, the situation may arise that this adjustment has to be repeated more frequently.

In a further aspect of the method and device according to the invention, it is derived from certain characteristics of the plethysmographic signal during a short interval in open-loop operation whether the servo-reference level is set correctly or too high or too low in order to subsequently adjust this level in the correct direction. It can also be derived from the values determined, how quickly the adjustment has to be repeated and to what magnitude the loop gain of the servo loop has to be set. The mentioned short interval can comprise some heart beats or preferably one heart beat. In this embodiment only one beat per twenty to forty heart beats is lost. This is not found to be inconvenient or disadvantageous for e.g. monitoring of patients while a fully reliable and correct servo-reference level is obtained.

In closed-loop operation a predetermined point on the wave form of the pressure signal, e.g. the beginning of arterial systole, is detected, whereupon the control loop is opened and the cuff pressure is adjusted at an intermediate value. This value can e.g. be an intermediate value between the last observed systolic and diastolic pressure or a fixed or variable value or swing above the diastolic pressure. Thereafter, in open-loop operation, the corresponding point is detected on the wave form of the plethysmographic signal, such as the beginning of one of the following systoles or of the following systole. Also the minimal or trough amplitude value and the maximal or peak amplitude value is determined in the plethysmographic signal. The loop is closed again after detection of the corresponding point in the plethysmographic signal, while the servo-reference level at the output of the integration circuit is adjusted at a value between the trough amplitude and the peak amplitude value. For, this value is at a fraction F of the peat-trough amplitude difference above the trough amplitude value.

Figures 6, 7:
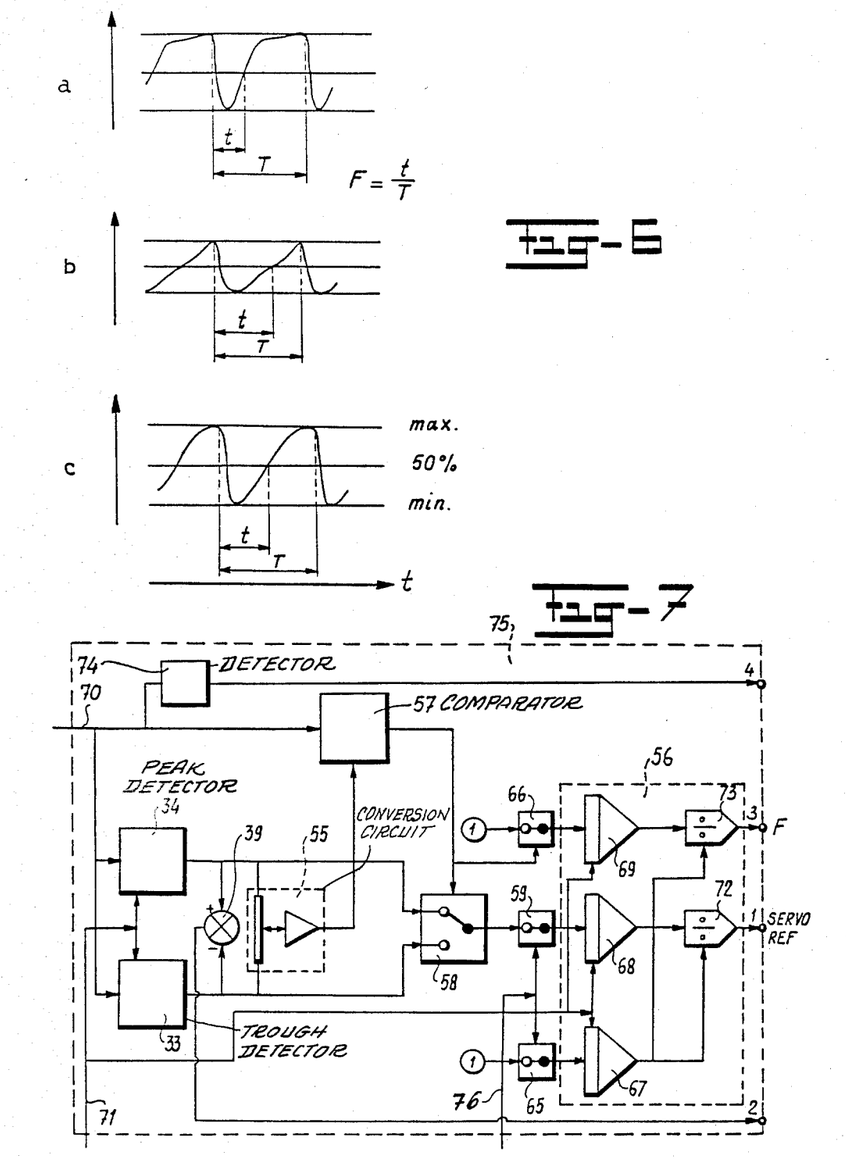
FIG. 6 shows three wave forms of the plethysmographic signal in open-loop operation for different values of adjusted cuff pressure.
FIG. 7 shows a diagram of a memory circuit according to the invention used in the electronic control circuit of the device.

The value for the fraction F can be derived from the form of the plethysmogram with reference to FIG. 6.

When the cuff pressure supplied during open-loop operation is relatively high with respect to the real intra-arterial pressure, then the artery will be collapsed for a relatively long time with respect to the duration of the period of the heart beat, and the plethysmogram will have the form shown in FIG. 6a. The servo-reference level was set at a relatively too high value. Due to this, this servo-reference level will now be adjusted in the direction of the minimal or trough amplitude value of the plethysmogram with a corresponding low value for the fraction F.

When the adjusted and supplied cuff pressure is relatively low with respect to the real intra-arterial pressure, then the arterty will be collapsed for a relatively short time with respect to the duration of the heart beat or not reach the level of full collapse. The latter will be accompanied by a relatively small amplitude of the plethysmographic signal as indeed appears from FIG. 6b (with respect to FIG. 6a). The servo-reference level was set at a relatively low value. The servo-reference level will now be adjusted in the direction of the maximal or peak amplitude value with a bigger value for the fraction F.

When the cuff pressure, adjusted and supplied in open-loop operation, was correct and also the servo-reference level, a plethysmogram as shown in FIG. 6c will follow. The fraction F can simply be measured from the wave form, a.o. by the time ratio $F = t/T$.

FIG. 7 shows a diagram of the relevant unit for the adjustment after a short interval, such as one heart beat, of the servo-reference level at the output of the memory circuit.

The plethysmographic signal inputted at 70 is supplied respectively to the parallel circuit of peak detector 34 and trough detector 33 and to a comparator circuit 57 which may be a reference value intersection detector. The peak detector 34 and trough detector 33 are switched on via a control signal on line 71, when the servo loop is opened. This opening may be effected by means of a separate detector for detecting the predetermined point such as the beginning of the upward stroke of systole. The separate detector is taken up at the detection circuit of peak detector and trough detector for the pressure signal.

A value between the peak and trough amplitude values is derived by means of a conversion circuit 55 succeeding the plet detectors. The value is supplied as a reference value to the intersection detector (comparator circuit) 57. The conversion circuit 55 can advantageously consist of a resistance divider having an adjustable tap and succeeding buffer amplifier. A fixed or variable intermediate value between the peak and trough amplitudes can be obtained in this way. Aternatively, the conversion circuit 55 can consist of a summing circuit and succeeding two-divider so that a (Plet$_{peak}$+Plet$_{trough}$)/2− signal is obtained.

The output signal of the detector (comparator) 57 is supplied as a switching signal to the switch 58. The output signal of this switch is supplied via a switch 59 to the input of the memory circuit 56 consisting of several integrators. These integrators are reset to zero at the beginning of the open-long interval by means of the control signal on line 71. Both the switch 59 in the input circuit of the integrator 68 and the switch 65 in the input circuit of the second integrator 57 are opened via a control signal on line 76 at the closing of the loop. Loop closing may be effected by the separate detector 74 for detecting the corresponding point in the next systole in the plethysmographic signal, e.g. at the beginning of the downward stroke.

When the plethysmographic signal in the intersection detector (comparator) 57 lies beneath the reference value during time t (FIG. 6), the peak amplitude value of the detector 34 is supplied to the integrator 68. When the plethysmographic signal in the intersection detector 57 lies above the reference value during the remaining time t-T, then the trough amplitude value of the detector 33 is supplied to the integrator 68. Also, the unity signal supplied during the period T is integrated in the second integrator 67, due to which as a measure for the time T a signal is provided at its output to be supplied to the divider 72 connected to the integrator 68. This provides, at the output of the memory circuit 56, for the servo-reference level being adjusted to a fraction F of the peak-trough amplitude difference above the trough amplitude value.

Also, the fraction F is determined separately by supplying the output signal of the intersection detector 57 as a switching signal to the switch 66 taken up in the input circuit of a third integrator 69. This causes the unity signal supplied to the integrator 69 to be integrated only during the time t, due to which after division by the time signal T in the second divider 73 at its output the said "time" fraction F is obtained.

Figure 8:
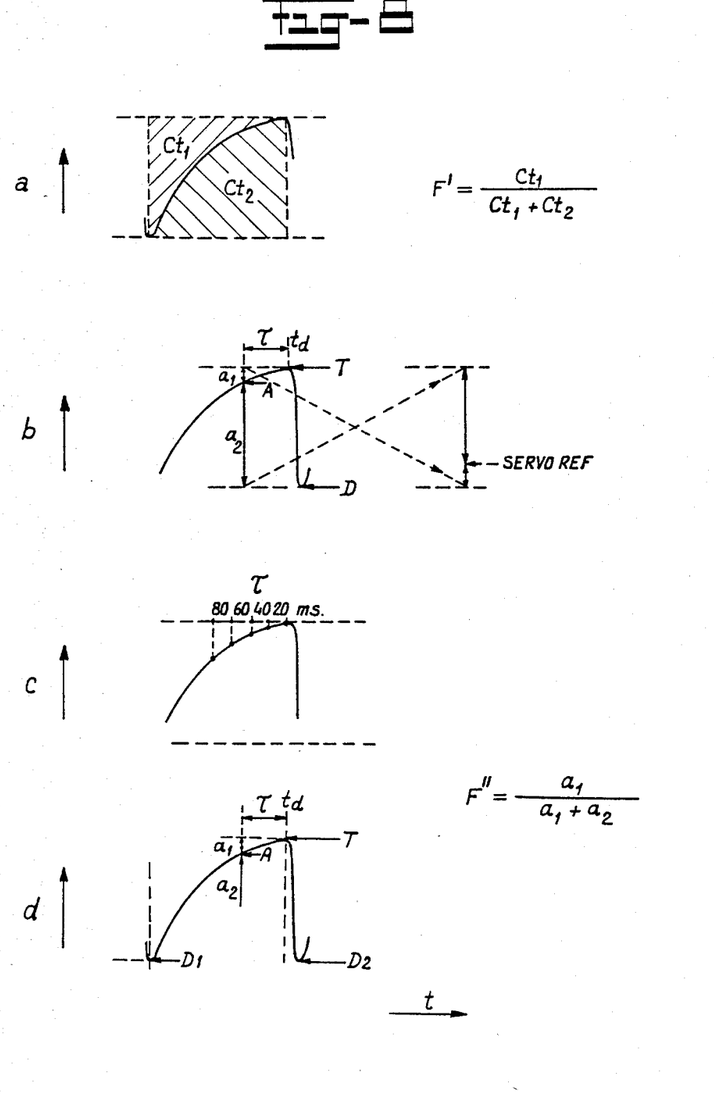
FIG. 8 shows some wave forms to explain the operation of the memory circuit.
Figure 9:
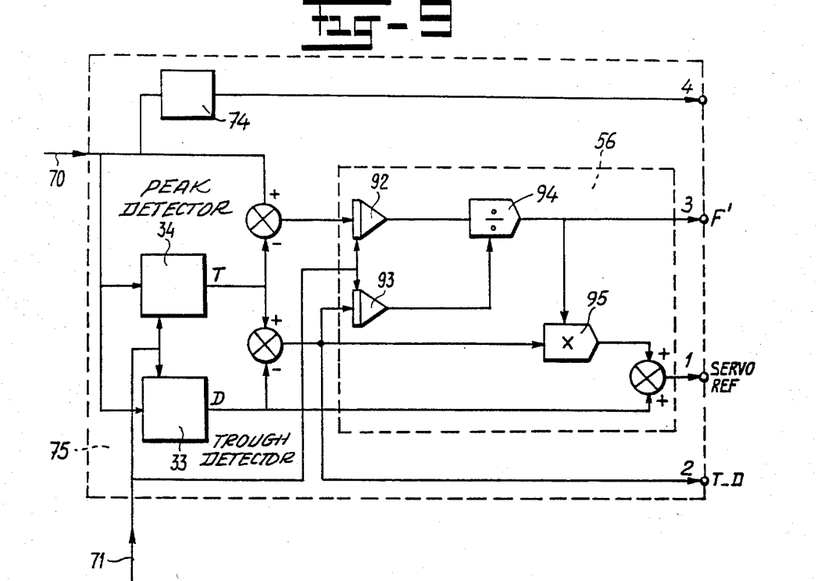
FIG. 9 shows a diagram of another memory circuit according to the invention used in the electric control circuit of the device.

FIG. 8a and FIG. 9 show in what other way the fraction can be determined as well. Based again on the plethysmographic signal, instead of a time ratio, now an area ratio can be used as criterium. This is shown in FIG. 8a, in which $$F = \frac{ct1}{ct1 + ct2}.$$

The memory circuit 56 in FIG. 9 comprises an integrator 92 to integrate the varying difference between the plethysmographic signal, applied at 70, and the peak amplitude value T from the peak detector 34. The constant difference between the peak amplitude value T and the trough amplitude value D from the trough detector 33 is integrated in the same time period in a further integrator 93. Division of the one integration signal in the divider 94 by the further integration signal produces the fraction F'. This fraction can be used for the adjustment by adding the peak-through amplitude difference T-D, multiplied in the multiplier 95 with the fraction F', to the trough amplitude value D. As a result of the integrating action, this "area" fraction will be somewhat less sensitive to disturbances in the wave form of the plethysmographic signal.

Finally, using an "amplitude" fraction as criterium appears to be the most sensitive and reliable method. Instead of a time ratio or an area ratio now an amplitude ratio is determined in a pulse period at a point of time which lies $\tau$ ms before the peak T of the wave form. This is indicated in FIG. 8b. The fraction value $$F'' = \frac{a1}{a1 + a2}$$

in which a1+a2 is the amplitude difference between the peak level T and the trough level D, and a1 is the amplitude difference between the peak level T and the level A of the plethysmographic signal at a time $\tau$ before the peak. Said peak occurs at the point of time $t_d$. $\tau$ may be a fixed value of e.g. 50 ms.

As at the end of the open-loop period the servo-reference value is adjusted to a (established) fraction above the trough amplitude, in this case the adjusted servo-reference value can be found in the figure by reversing the amplitude ratio along the vertical. This is indicated in the right portion of FIG. 8b.

To be on the safe side one can average for a number of values by taking two or four values for $\tau$ (see FIG. 8c) and by dividing the result by 2 or 4.

Figure 10:
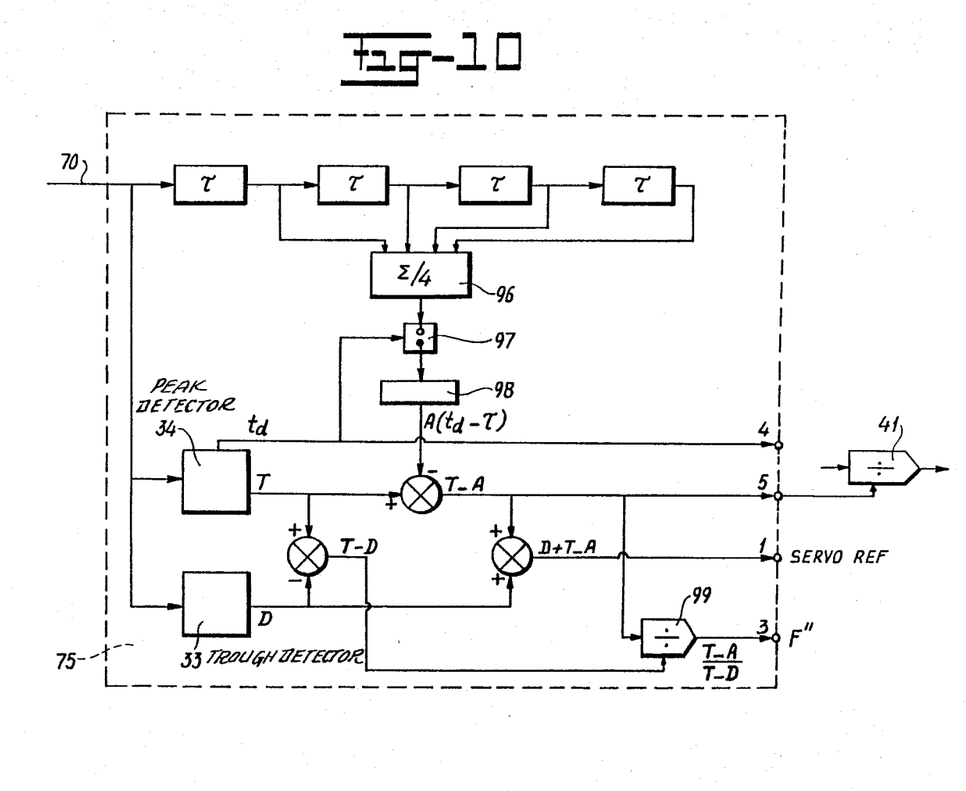
FIG. 10 shows a diagram of still another memory circuit according to the invention used in the electronic control circuit of the device.

It has little or no consequence on the determination of the fraction if the trough value D1 of the previous stroke is taken instead of the trough value D2 of the present stroke (see FIG. 8d). As the point of time $t_d$ is not known in advance, a delay line $\tau$ or a number of delay lines $\tau$ each of e.g. 20 ms, is used for the plethysmographic signal as indicated in FIG. 10. The averaged level value A at the output of the averaging circuit 96 is inputted in the memory 98 at the time $t_d$ (via the switch 97), that means at the beginning of the downward stroke in the plethysmogram. The switch 97 and the memory 98 constitute a sample-and-hold circuit.

The following relations apply:

$$a1 = T - A \text{ and } F \frac{a1}{a1 + a2} = \frac{T - A}{T - D},$$

for the servo-reference level applies: servo ref=−D+a1=D+T−A, for the gain factor G in the servo loop applies: G=F''.(T−D)=T−A (apart from a constant).

In FIG. 10 it is indicated in what manner the various signals at the output of the unit are obtained with the aid of some adder/subtractors. Said outputs 1, 3, 4, 5 respectively supply the adjusted servo-reference level, the fraction value, the gain factor for the setting circuit 41 (FIG. 5) and the detection signal indicating the beginning at $t_d$ of the downward stroke.

By using a microprocessor control it is possible to advantageously store samples in a memory also at other times than at the beginning of a systole in the pressure signal or the plethysmographic signal respectively. Subsequently, the computation can be carried out on this basis. A suitable moment for opening the control loop is e.g. when the pressure signal in downward direction passes the level halfway between the systolic and diastolic pressure. This applies also for closing the control loop again, but then on the basis of the plethysmographic signal. By opening and closing the control loop at these times a smooth course of the pressure curve is obtained.

Figure 11:
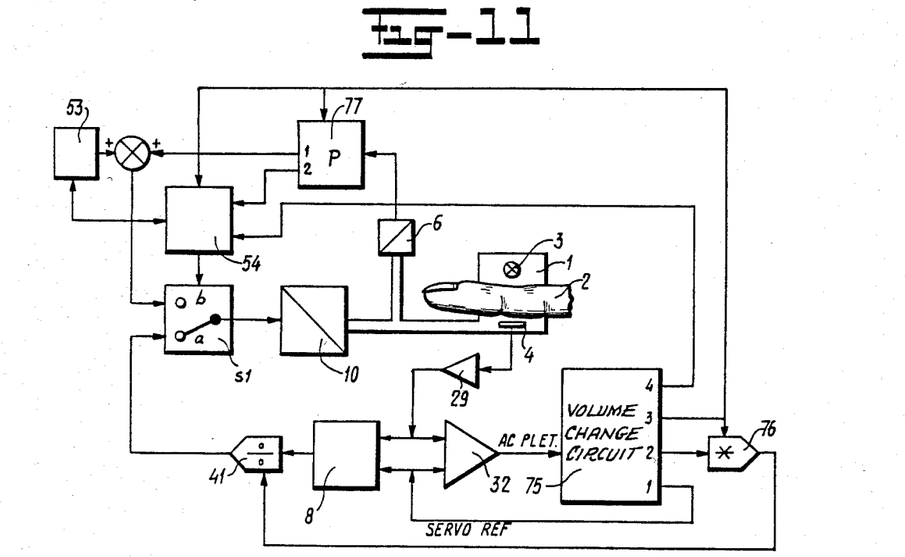
FIG. 11 show a diagram of another embodiment of the device according to the invention.

FIG. 11 shows a diagram of a further embodiment of the invention. The volume-change unit according to FIGS. 7, 9 or 10 represented by block 75 is used in this embodiment. The adjusted servo-reference level from the output 1 of this V unit is supplied to the inputs of the differential circuit 32 and the PID circuit 8. Also, the fraction signal from the output 3 of the unit 75 is supplied to the timing circuit 54. A typical normal value for the fraction at a correct, preceding servo-reference level and, therefore, blood pressure level is 0.25. When the computed fraction deviates substantially from this, it is decided in the timing circuit that a deviation has come about which possibly cannot be adjusted in one heart beat period, so that an increased frequency of adjustment is required. Normally, an adjustment of once per twenty to thirty seconds can be established in the timing circuit. In case of fraction values smaller than a predetermined value, e.g. 0.15 or bigger than a predetermined value, e.g. 0.4, the interval up to the next adjustment can be reduced to five through ten seconds. If required, the adjustment frequency can be set at a more gradual course in the timing circuit 54. In case a drift has occurred in the servo-reference level due to whatever cause, then it can be adjusted in this accelerating manner.

In the known method and device the loop again in the PID control loop is set inversely proportional to the peak-trough differential amplitude in the plethysmographic signal in open-loop operation. In consequence of this, the loop gain is adapted to the various sensitivities of the individual persons and of the various photoelectric plethysmographs. An improvement of this adaptation is obtained when in the multiplier 76 the product is formed of the fraction signal and the peak-trough amplitude difference taken from the output 2 of the unit 75. For, it is possible that due to a preceding de-adjustment of the servo-reference level, the blood pressure is estimated so low that a sub-maximal plethysmographic pulsation is measured in open-loop operation. At the same time the measured fraction value is the relatively large, typically in the range of 0.5 instead of the target value of 0.25. A compensation is obtained by multiplication of the two quantities so that high frequency oscillations as a result of a high loop gain, caused in this state, are prevented.

In the pressure-change unit 77 succeding the pressure transducer 6 a pressure value in between the peak and trough amplitude values is determined in the conversion circuit (FIG. 5) succeeding the detectors 83, 84, which pressure value is provided at the output 1.

This intermediate value can be an average value halfway between the peak and trough amplitude values. It can, howver, also be a fixed swing value above the diastolic or trough amplitude value. The swing value can, however, be advantageously adjusted variably in dependence each time of the last determined magnitude of F, F' or F". It is advantageous thereby to start only from the diastolic pressure value as this value is more stable and varies less than the systolic pressure value. The diastolic pressure value also does not drop so low at collapse.

The predetermined point of the pressure signal, such as at the beginning of arterial systole, is also determined in the P unit 77 via a separate detector, when this pressure changes from slowly dropping to rapidly rising. This latter initial-rising stroke signal is supplied from the output 2 of the P unit to the timing circuit 54.

This separate detector can be an intersection detector respensive to the zero-intersection of the first derivative of the pressure signal. Also the beginning of each heart beat can be established by means of an algorithm taken up in a controlling microprocessor. The momentary heart frequency can be computed as $60/T_d$ in beats per minute from the time $T_d$ between two successive corresponding points of time. As already indicated before, only the pulsating plethysmographic signal can be observed in the short interval in open-loop operation for the adjustment and not the blood pressure pulsation. The beginning of the heart beat can also be established on the basis of this plethysmographic signal in the same way be means of the detector 74 shown in FIGS. 7 or 9 or by means of the peak detector 34 shown in FIG. 10. The signal from such a detector is supplied via the output 4 of the unit 75 to the timing circuit 54, so that a beat-to-beat computation of the heart frequency—not interrupted by the adjustment—is obtained. A heart beat counter taken up in the timing circuit 54 determines the heart frequency from the supplied pulses.

The counter resets the timing circuit 54 at every pulse and counts the number of beats up to the moment of switching of the state switch S1 from a to b. This number of beats may vary in dependence of the preceding value of the fraction value. At the moment of switching to open-loop operation the unit 75 is activated via the signal 71. The newly adjusted servo-reference level, the fraction value, the peak-trough differential amplitude of the plethysmographic signal and the beginning of systole in the plethysmographic signal where this changes from slowly rising to rapidly falling, are then determined in the V unit 75. The control loop is closed by the state switch S1 when this latter time of the beginning of systole in the plethysmographic signal is reached. The loop gain (FIGS. 10,11) is set on the basis of the product of peak-trough amplitude and fraction value supplied to the setting circuit 41.

As described in Netherlands patent application No. 81,04879, it can occur in certain situations of monitoring of patients that the blood pressure has to be watched, while the heart has been stopped temporarily. E.g. during open-heart operation or when due to other causes no peripherial pulse pressure in a finger can be perceived. Normally, in the adjustment procedure, use is made of a constant cuff pressure between systolic and diastolic pressure and of a pulsating intra-arterial pressure. In case this pulsation fails, it is also possible to superpose an external pressure pulsation on the fixed cuff pressure such that still a pulsating transmural pressure difference and, thus a pulsating plethysmographic signal, is obtained. As described in the abovementioned Netherlands patent application the artificial pulsations are introduced inversely, i.e. falling in systole and rising in diastole. This required wave form can be obtained from a simulator as described in Med. Biol. Engineering (1973) pages 214–216. However, also a stylized wave form can be presented in the form of a saw tooth, e.g.

with a rising time in diastole of 0.5 sec. and a falling time in systole of 0.1 sec. having a peak to peak value of 60 mm Hg. This pulsation is then superposed onto the cuff pressure maintained on the last perceived, average pressure value.

When, due to one of the abovementioned causes, the heart beats are failing in the pressure signal, there are no initial rising stroke pulses being supplied to the heart beat counter in the timing circuit 54. A watching circuit taken up in the timing circuit detects this absence and starts, after a predetermined time, e.g. ten to twenty seconds, an external simulator 53. In this case the state switch S1 is also switched via the heart beat counter. The pressure signal of the P unit 77 is now made equal to the average cuff pressure. The simulation signal is superposed hereto in the right phase, so that a normal pulsation in the transmural pressure is obtained though. The V unit 75 determines in the usual way the various levels and times after which the loop is closed.

Figure 12:
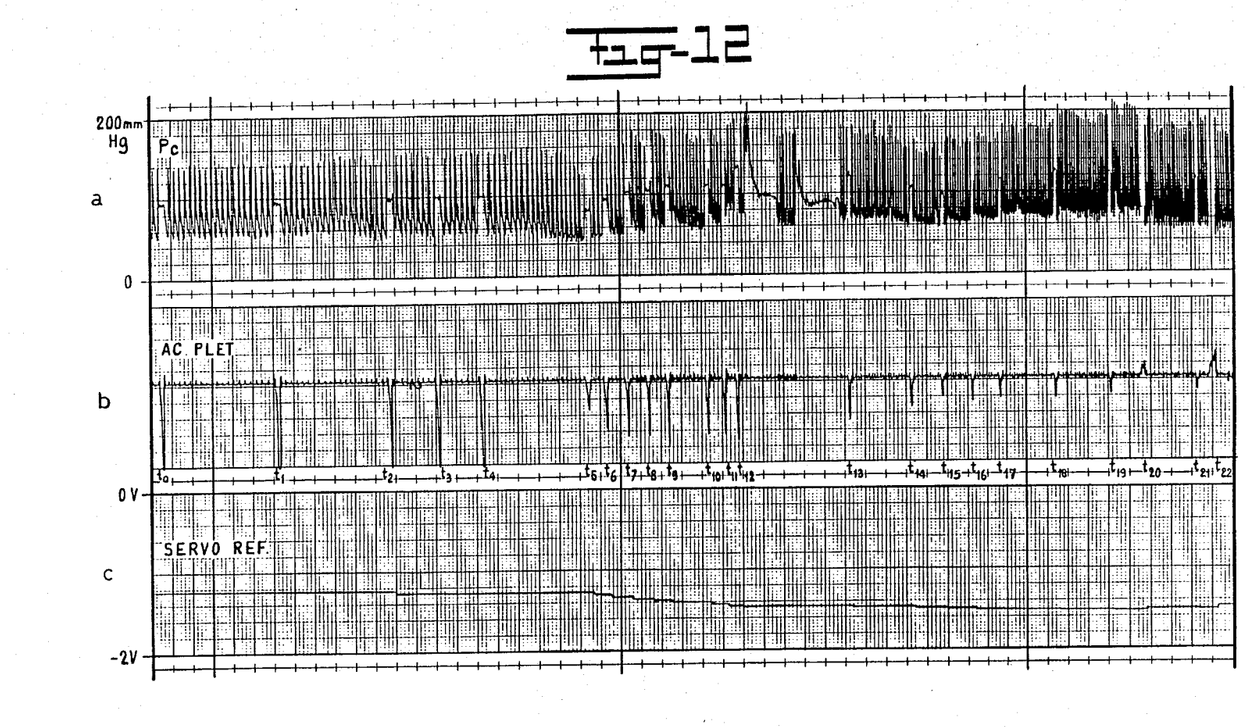
FIG. 12 shows recorded wave forms to explain the invention.

FIG. 12 shows some recorded wave forms when measuring the blood pressure in the finger of a patient. FIGS. 12a, 12b and 12c show the cuff pressure, the plethysmographic signal and the servo-reference level respectively. The recording of the cuff pressure Pc also shows the heart beat frequency of the patient indicating that the patient, when awaking ($t_7$–$t_{10}$) gradually gets a higher frequency in this case. The intervals each time of one heart beat, in which the servo-reference level in open-loop operation is adjusted, are clearly visible. It is also clearly visible that the point of switching is halfway the peak-trough amplitude difference. The number of heart beats, after which adjustment in one beat is effected, is dependent on the magnitude of the last-found fraction value.

The ac-plethysmographic signal shown in FIG. 12b represents, in the negative going peaks (in the direction of more light transmission in the finger) at times t0, t1 . . . t22, the wave forms at the end of which the servo-reference level shown in FIG. 12c is adjusted. At times t0 and t1, a negligible deviation of the fraction with respect to the nominal value is found and the number of beats up to the next adjustment amounts to twenty. At t2, indeed a deviating fraction value is found and the number of beats up to the next adjustment amounts to ten. At t5 a large fraction value is found at a small amplitude value of the plethysmogram.

The two disturbances present in the cuff pressure between t12 and t13 are caused externally, namely the inflation of a proximal cuff, and are not important.

It is obvious that the invention is not limited to the represented embodiments of the method and device, but that modifications and additions are possible within the scope of the invention. The above/described method steps, for instance, can be carried out, but with the embodiments described above, also with a microcomputer.

Figure 13:
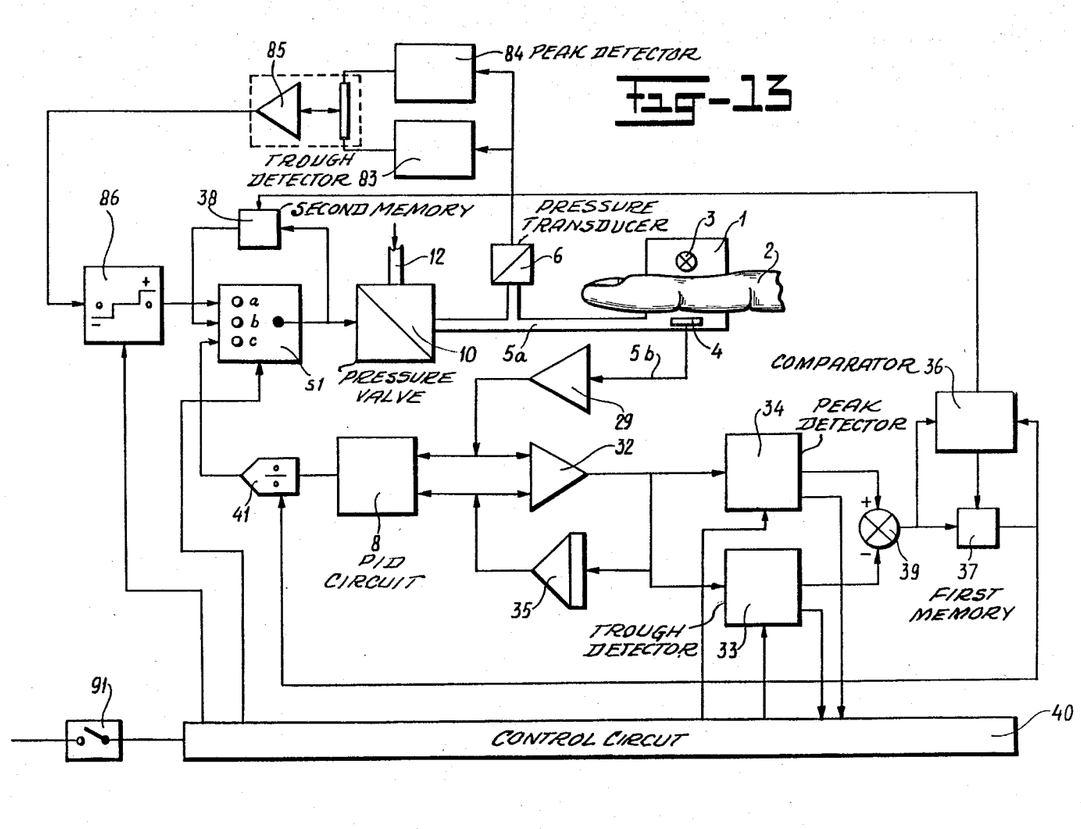
FIG. 13 shows a diagram of a further embodiment of the device according to the invention.

A further embodiment is also possible based on the assumption that that the servo-reference level and the cuff pressure are approximately correct as long as the shift in the initially correctly adjusted reference level has—for whatever reason—not yet progressed far. A variation is then introduced represented by two or three pressure levels around the cuff pressure last measured in closed-loop operation, whereby in open-loop operation the maximal plethysmographic amplitude is selected. Subsequently at the pressure level, whereby the largest amplitude difference is found, the associated average plethysmographic level is established and the control loop is closed.

FIG. 13 shows this embodiment, which only in part resembles the device of the Netherlands patent application mentioned before. At the moment of adjustment, the device is brought from the closed-loop state in position c of the state switch S1 into the open-loop state in position a under the control of the control circuit 40. A pressure value obtained halfway of the peak-trough difference amplitude of the pressure signal is supplied from the parallel circuit of peak detector 84 and trough detector 83 via the conversion circuit 85 to a step generator 86. This generator is controlled by the logic control circuit 40 and processes the supplied signal such that first the average cuff pressure minus a fixed value, e.g. 15 or 20 mm Hg or 0.2× the average pressure, subsequently the average pressure and after that the average pressure plus a fixed value, e.g. 15 or 20 mm Hg or 0.2× the average pressure, is supplied to the state switch S1. The peak-trough amplitude of the plethysmographic signal is determined at each pressure value, supplied via position a, and that pressure value, at which the largest amplitude is perceived, is maintained.

The plethysmographic signal is supplied via the amplifier 29 and the differential amplifier 32 to the parallel circuit of peak detector 34 and trough detector 33. The differential amplitude obtained from the differential circuit 39 is supplied to a first memory circuit 37 which is initially at zero. A comparator circuit 36 compares each time the new differential amplitude with the preceding one and when exceeding it the current pressure value at the output of the state switch S1 is taken over in a second memory circuit 38. The new differential amplitude is taken over in the first memory circuit 37 and the peak detector and trough detector are reset under control of the logic control circuit 40. The cuff pressure is increased with the step value and the process is repeated. The second memory circuit 38 remembers the pressure level at which the plethysmographic signal occurred with maximal amplitude difference.

Hereafter the device is put into position b of the state switch for e.g. three seconds. In this short interval the memory or integration circuit 35 can adjust its output value or servo-reference level, while the cuff pressure found is maintained during this period of time.

After this short interval the device is put into position c of the state switch and the closed-loop operation is restored.

It is also possible, instead of a stepwise variation of the cuff pressure, to vary the servo-reference level stepwise. It is then established at what level thereof the largest pressure amplitude occurs, or at what ever-increasing servo-reference level the device just does not become unstable. This method is somewhat less exact.

Besides the fact that the known device only needs a relatively slight extension, namely two top detectors 83, 84 for the pressure signal and a timing circuit 91, there is the advantage that relatively large deviations can be corrected in one search period. A disadvantage, however, is that the aimed continuous measurement of the blood pressure is frequently interrupted by adjusting intervals of five to six seconds duration.

I claim:

1. A method for correcting the cuff pressure in a plethysmographic arrangement for the indirect, non-invasive and continuous measurement of blood pressure in a body extremity by using a plethysmograph in a fluid-filled pressure cuff to be wrapped about said extremity, an electronic control circuit connected to the plethysmograph, and an electric pressure valve and a pressure transducer connected to said cuff, the cuff pressure being controlled by a plethysmographic signal from said plethysmograph in closed-loop operation with the aid of a servo-reference level obtained via a memory circuit in the control circuit, which servo-reference level is initially adjusted such that the cuff pressure corresponds substantially with the momentary arterial pressure, said method comprising the steps of:

opening the closed loop of the control circuit for a short interval, in open-loop operation, adjusting the cuff pressure with the pressure valve at an intermediate pressure derived from the pressure last measured at the pressure transducer, and adjusting the servo-reference level via the memory circuit.

2. A method according to claim 1, wherein the step of adjusting the servo-reference level is carried out at regular time intervals.

3. A method according to claim 1 wherein the step of adjusting the servo-reference level comprises the step of adjusting the servo-reference level as a function of the shape of the plethysmographic signal, influenced by the magnitude of the deviation of the cuff pressure, adjusted in open-loop operation, with respect to the real arterial pressure.

4. A method according to claim 3, wherein the step of adjusting cuff pressure during open-loop operation comprises the steps of:

determining peak and trough amplitude values of the plethysmographic signal during open-loop operation deriving an intermediate value between the peak and trough values, such as an average amplitude value, and integrating the peak and trough amplitude values respectively during that part of the plethysmographic signal that is below and above this intermediate value, and dividing by the pulse period, by which the servo-reference level is adjusted to be a fraction of the peak-trough amplitude difference above the trough amplitude value.

5. A method according to claim 4, wherein the fraction is determined separately by integrating a unity signal during that part of the plethysmographic signal that is below the intermediate amplitude value, and by subsequently dividing by the pulse period.

6. A method according to claim 3, wherein the step of adjusting the servo-reference level comprises the steps of:

determining peak and trough amplitude values of the plethysmographic signal in open-loop operation, in one pulse period at a point of time before the peak amplitude, determining the difference between peak amplitude value and plethysmographic signal and dividing by the peak-trough amplitude difference, and adding the fraction value thus obtained to the trough amplitude value to provide the adjusted servo-reference level.

7. A method according to claim 3, wherein the step of adjusting the servo-reference level comprises the steps of:

determining peak and trough amplitude values of the plethysmographic signal in open-loop operation, in one pulse period integrating the varying difference between plethysmographic signal and peak amplitude value providing a first integration signal, simultaneously integrating the constant peak-trough amplitude difference providing a second integration signal, and multiplying the peak-trough amplitude difference with a fraction value obtained by dividing the first integration signal by the second integration signal and then adding their fraction to the trough amplitude value to provide the adjusted servo-reference level.

8. A method according to claim 7, wherein the loop gain in the control circuit is set inversely proportional to the peak-trough amplitude difference of the plethysmographic signal in open-loop operation, and wherein the peak-trough amplitude difference is first multiplied with the said fraction before being used for the setting of the loop gain in the control circuit.

9. A method according to claim 7 wherein when the obtained fraction value deviates more than a predetermined value from the fraction, the frequency of adjustment is increased.

10. A method according to claim 6, wherein the step of determining the difference between peak amplitude and plethysmographic signal at a point in time comprises the step of making that determination at a time chosen in a sub period of 20 to 80 ms before the peak amplitude of the plethysmographic signal.

11. A method according to claim 9, characterized in that the frequency of adjustment is gradually changed.

12. A method according to claim 1 wherein peak and trough amplitude values of the pressure signal are determined in closed-loop operation, and wherein the moment of switching from closed to open-loop operation and back respectively occurs synchronously with the heart beat on the basis of the pressure signal in closed-loop operation and on the basis of the plethysmographic signal in open-loop operation respectively.

13. A method according to claim 11, wherein in closed-loop operation the beginning of arterial systole is detected after which the closed loop of the control circuit is opened, and in open-loop operation the beginning of the next arterial systole is detected after which the open loop of the control circuit is closed and the adjusted servo-reference level is inputted in the control circuit.

14. A method according to claim 12 further comprising the step of using the signals, derived from the pressure signal in closed-loop operation and from the plethysmographic signal in open-loop operation and required for switching synchronously with the heart beat, for counting the heart beat.

15. A method according to claim 12, wherein in open-loop operation the cuff pressure is adjusted to an average pressure between the peak and trough amplitude values last measured at the pressure transducer.

16. A method according to claim 12, wherein in open-loop operation the cuff pressure is adjusted to a swing value above the trough amplitude value last measured at the pressure transducer.

17. A method according to claim 16, wherein the swing value is adjusted in dependence of the fraction value last obtained, 18. In a plethysmographic arrangement for the indirect, non-invasive and continuous measurement of the blood pressure in a body extremity, including a plethysmograph in a fluid-filled pressure cuff for wrapping about said extremity, an electric pressure connected to said cuff, and an electronic control circuit connected to said plethysmograph provided with a control loop having a differential amplifier and memory circuit in the feedback circuit for the servo-reference level, and with a control loop having a proportionate, integrate, and differentiate (PID) circuit, a parallel circuit of peak detector and trough detector connected to the pressure transducer for a pressure signal, which parallel circuit is responsive to the pressure in the pressure cuff and a state switch connected to the pressure valve for closed-open loop operation, the improvement comprising: a conversion circuit following the peak detector and trough detector for the pressure signal which derives an intermediate value from the peak and/or trough amplitude values of the pressure signal in closed-loop operation, and a timing circuit which switches the state switch for a short interval from closed-loop position to open-loop position, in which interval said intermediate value is supplied via the state switch to the electric pressure valve, and said memory circuit which adjusts the servo-reference level such that the average difference at the differential amplifier is zero.

19. A device according to claim 18, wherein the memory circuit comprises an integration circuit.

20. A device according to claim 18, wherein the timing circuit is implemented such that it puts at regular time intervals the state switch for a short interval in open-loop position, due to which the servo-reference level is adjusted regularly.

21. A device according to claim 18, wherein the control loop having a differential amplifier and memory circuit further comprises a parallel circuit of peak detector and trough detector for the plethysmographic signal, and wherein the parallel circuit of peak detector and trough detector for the plethysmographic signal is followed by a further conversion circuit, which derives from the peak and trough amplitude values of the plethysmographic signal an average reference value, such as half the peak-trough amplitude difference, and a comparator circuit to establish when the plethysmographic signal is below and above the reference value respectively in order to enable the memory circuit to integrate with respect to time the peak amplitude and the trough amplitude, so that at the output of same the servo-reference level, adjusted at a fraction (F) of the peak-trough amplitude difference above the trough amplitude value, is provided.

22. A device according to claim 21, wherein the comparator circuit comprises an intersection detector to establish when the plethysmographic signal intersects the level of the reference value, and a switch controlled by the output signal of the intersection detector in an input circuit of the memory circuit, the switch having first and second in parts respectively connected to the peak detector and to the trough detector of the plethysmographic signal.

23. A device according to claim 22, wherein the memory circuit comprises a first integrator connected to the output of the switch and followed by a divider, and a second integrator receiving a unity signal, the output signal of which second integrator is supplied to the divider as direct measure for the pulse period duration.

24. A device according to claim 23, wherein the memory circuit further comprises a third integrator receiving the unity signal, in the output circuit of said third integrator a second divider is taken up, to which the output signal of the second integrator is supplied and in the input circuit of said third integrator a second switch is inserted, which second switch is controlled by the output signal of the intersection detector, the output of the second divider at which the said fraction (F) is obtained.

25. A device according to claim 21, wherein the parallel circuit of peak and trough detector for the plethysmographic signal is followed by a subtractor circuit, and the PID circuit being followed by a gain setting circuit influenced by the peak-trough amplitude difference wherein a multiplier, connected to the subtractor circuit, is provided in which the peak-trough amplitude difference is multiplied with the fraction and is then supplied to the gain setting circuit.

26. A device according to claim 18, wherein the control loop having a differential amplifier and memory circuit further comprises a parallel circuit of peak detector and trough detector for the plethysmographic signal followed by a subtractor circuit, wherein the memory circuit comprises an integrator which integrates the varying difference between the plethysmographic signal and the peak amplitude value of same to form a first integration signal; a second integrator which integrates during the same time, the constant peak-trough amplitude difference to form a second integration signal, a divider which obtains a fraction (F') by dividing the first integration signal by the second integration signal, which fraction is multiplied in a multiplier with the constant peak-trough amplitude difference, the multiplication signal being added to the trough amplitude value thus providing the adjusted servo-reference level (FIG. 9).

27. A device according to claim 18, wherein the control loop having a differential amplifier and memory circuit further comprises a parallel circuit of peak detector and trough detector for the plethysmographic signal followed by a subtractor circuit, wherein the memory circuit comprises at least one delay line followed by a sample and hold circuit, the output of which and the peak amplitude value are supplied to a second subtractor circuit, the output of which and the trough amplitude value are supplied to an adder circuit, the output of which thus providing the servo-reference value adjusted at a fraction (F") of the peak-trough amplitude difference above the trough amplitude value.

28. A device according to claim 27, wherein the output of the second subtractor circuit is supplied to a divider in which it is divided by the peak-trough amplitude difference, said fraction value (F") being obtained at the output of the divider.

29. A device according to claim 18, wherein a first detector responsive to the pressure signal in closed-loop operation which detects a given point in the stroke, and a second detector responsive to the plethysmographic signal in open-loop operation which detects the corresponding point in the next stroke in order to open and to close the loop in the control circuit synchronously with the heart beat.

30. A device according to claim 29, wherein that first detector detects in the pressure signal the beginning of the rising stroke of arterial systole, and the second detector detects in the plethysmographic signal the beginning of the downward stroke of the next arterial systole.

31. A device according to claim 29, wherein the output signals of the first and second detector respectively are supplied to the timing circuit in order to switch the state switch during one beat from closed- to open-loop operation and back synchronously with the heart beat, and the timing circuit, on the basis of the deviation of a fraction value of a nominal value thereof, establishes after how many heart beats the switching to open-loop operation for the adjustment of the servo-reference level has to take place.

32. A device according claim 29, wherein the timing circuit is provided with a heart beat counter in order to establish, on the basis of the output signals of the first and second detectors, the momentary heart beat frequency in beats per minute both in closed and in open-loop operation.

33. A device according to claim 32, wherein a pulsation simulator is provided to introduce artificial pressure pulsations in the control circuit when natural arterial pressure pulsations are absent, and wherein the timing circuit is provided with a watching circuit in order to switch on, in absence of heart beats after a predetermined time, e.g. 10-20 seconds, the pulsation simulator, of which the artificial pressure pulsation is superposed in the correct phase on the intermediate pressure value supplied in open-loop operation to the state switch.

* * * * *